United States Patent [19]

Lerner et al.

[11] Patent Number: 5,716,855
[45] Date of Patent: Feb. 10, 1998

[54] FLUORESCENT LATEX CONTAINING AT LEAST TWO FLUOROCHROMES, PROCESS FOR PRODUCING IT AND APPLICATION THEREOF

[75] Inventors: Dan Lerner; Frédéric Ricchiero, both of Montpellier; Joël Richard, Chantilly; Dominique Teychenne, Aubervilliers; Sophie Vaslin, Bry-sur-Marne, all of France

[73] Assignee: Societe Prolabo, France

[21] Appl. No.: 586,673

[22] PCT Filed: Nov. 7, 1994

[86] PCT No.: PCT/FR94/00867

§ 371 Date: Mar. 1, 1996

§ 102(e) Date: Mar. 1, 1996

[87] PCT Pub. No.: WO95/02635

PCT Pub. Date: Jan. 26, 1995

[30] Foreign Application Priority Data

Jul. 12, 1993 [FR] France ................... 93/08573

[51] Int. Cl.⁶ .................. G01N 21/64; G01N 33/533; C09K 11/02
[52] U.S. Cl. .................. 436/533; 436/172; 436/800; 523/200; 523/201; 252/301.35; 424/9.61
[58] Field of Search .................. 436/533, 172, 436/800; 523/200, 201; 252/301.35; 424/7.1

[56] References Cited

U.S. PATENT DOCUMENTS 4,342,739  8/1982  Kakimi et al. ............. 424/1
5,264,960 11/1993  Glance ...................... 359/344
5,369,036 11/1994  Mercolino et al. ........ 436/523
5,393,527  2/1995  Malick et al. ............. 436/532
5,607,864  3/1997  Ricchiero et al. ......... 436/533

FOREIGN PATENT DOCUMENTS

A-0 280 556  2/1988  European Pat. Off. .
WO-A-9110893  1/1991  WIPO .

OTHER PUBLICATIONS

IEEE Photonics Technology Letters, vol. 5, No. 6, Jun. 1, 1993, pp. 657–660.

Center For Broadband Telecommunications, 10 GBIT/S Wavelength Converter Realised by Monolithic Integration of Semiconductor Optical Amplifiers and Michelson Interferometer, pp. 67–70.

IEEE Photonics Technology Letters, vol. 6, No. 1, Jan. 1994, pp. 53–55.

IEEE Photonics Technology Letters, vol. 4, No. 10, pp. 1168–1171.

*Primary Examiner*—Tae Yoon
*Attorney, Agent, or Firm*—Blakely Sokoloff Taylor & Zafman

[57] ABSTRACT

A fluorescent latex with particles containing at least one encapsulated hydrophobic fluorochrome A (acceptor) and at least one encapsulated hydrophobic fluorochrome D (donor), wherein A is different from D and exposure to light radiation enables the emission from fluorochrome D to excite fluorochrome A, and a method for producing said latex and its use as a marker, particularly a biological marker, are also disclosed.

19 Claims, No Drawings

FLUORESCENT LATEX CONTAINING AT LEAST TWO FLUOROCHROMES, PROCESS FOR PRODUCING IT AND APPLICATION THEREOF

The present invention relates to a flourescent latex the particles of which contain at least two encapsulated hydrophobia fluorochromes. The invention also relates to a process for the preparation of the said latex and to the application of the latter as a marker, particularly a biological marker.

The latices are aqueous dispersions of polymer particles whose size is generally between 0.05 micron and several microns. On account of their particulate appearance, latices offer a large specific surface, which is exploited advantageously in a large number of applications and particularly in the paper, paint, magnetic tape and recording industries and in biology.

In biology, standard assay techniques use latices by way of support for markers of enzymic or radioisotopic type, so as to allow the quantitative assay of the species present in the medium to be analyzed.

This assay technique by molecular marking using, for example, a radioactive isotope, is extremely precise, reliable and is of great detection sensitivity. However, it has several drawbacks associated with the dispersion of the radioactive sources, the prolonged exposure of the personnel, the variation over time of the emission of the source associated with the half-life of the element and especially with the need, at the end of the analysis to isolate the free reagents from the complexed reagents. Radioactive emission is, in effect, entirely insensitive to the environment of the marker.

For the abovementioned reasons, the technique of analysis by fluorescence has established itself as the most effective alternative for the replacement of these conventional markers.

Fluorescent marking has many advantages when compared with radioactive marking. There is no risk of exposure to radiation. Fluorescent marking has excellent stability over time and it especially gives a finer response on account of the specificity of the emission of fluorescence to certain environmental parameters. There is thus no need to carry out post-analysis separations when it is used.

Nevertheless, the practical use of fluorescence particularly in biological assays (immunology, cell counting, flow cytometry) requires certain problems to be solved.

The fluorescence obtained by simple molecular grafting is of insufficient sensitivity as regards generalized practical application. It is difficult to detect this fluorescence when the concentration of the species present in the medium is less than $10^{-9}$ mol/liter. This considerably limits the use of this technique.

In order to be satisfactory, the sensitivity of the fluorescence should be comparable with that of radioactive marking, which would involve being able to work at concentrations of between $10^{-12}$ and $10^{-15}$ mol of particles per liter.

Moreover, the medium in which the compounds to be assayed are present may interfere with the fluorescence emitted by the fluorochromes (for example Rayleigh or Raman scattering of the water). There are a good many other compounds present, particularly in biological serum, which, under the effect of excitation by light radiation, also emit within a range from 300 to 500 nanometers. It is thus desirable for the fluorescence analysis signal to be above 500 nanometers with the widest possible spectral spacing between excitation and emission.

However, it is known that many lasers commercially available have a wavelength which is precisely between 300 and 500 nanometers; for example, the argon laser emits at 488 nanometers and the helium-cadmium laser emits at 440 nanometers. It is thus desirable to be able to choose a spectrum of excitation based on these wavelengths, even if this causes the spurious excitation of water or of other biological substances, provided that the emission of the latex is shifted towards longer wavelengths.

The very object of the present invention is indeed to overcome these drawbacks and/or to solve the problems mentioned above.

Other advantages afforded by the present invention will also become apparent on reading the description which follows.

Firstly, the invention relates to a fluorescent latex the particles of which contain at least one hydrophobic fluorochrome A (acceptor) and at least one hydrophobic fluorochrome D (donor) which are encapsulated, A being different from D and the emission of the fluorochrome D making it possible, under the action of light radiation, to excite the fluorochrome A.

By the term encapsulated, it is understood that the fluorochromes are almost entirely absent from the surface of the particles. They are essentially concentrated inside the polymer particles so as to leave the external surface of these particles available.

The fluorochromes according to the invention are selected so as to cover in emission the four main areas of the light spectrum, namely blue (400–500 nm), green (500–550 nm), yellow (550–600 nm) and red (600–750 nm).

Besides the required spectral properties, these fluorochromes also satisfy the following requirements:

They are hydrophobic, so as to promote their insertion into the particles of the latex and to be free of any subsequent release.

They have an affinity for the interior of the particle, that is to say that they are chemically compatible with the polymer constituting the latex particles and, where appropriate, with the chemical functions present in this polymer. This compatibility plays a part during the synthesis of the corresponding fluorescent latex.

Lastly, bearing in mind their biological use, these fluorochromes are chemically and photochemically stable.

Among the fluorochromes which are suitable for the-invention, mention may be made more particularly of 9,10 diphenyl-anthracene (9,10 DPA), 9,10 bis-phenyl-ethynyl-anthracene (9,10 BPEA), 1,8 dichloro 9,10 bis-phenyl-ethynyl-anthracene. (1,8 $Cl_2$-9,10 BPEA), 5–12 bis-phenyl-ethynyl-naphthacene (5,12 BPEN), 6,13-bis (phenyl-ethynyl)pentacene, tetrabenzo(de,hi,op,st)pentacene, Coumarin 153, Nile red, 1,4-di[2(5-phenyloxazolyl)]-benzene or POPOP, 1,4-di[4-methyl-5-phenyl-2-oxazolyl]benzene or DM-POPOP, and tetraphenylporphyrine or TPP.

In general, the fluorochrome pairs or trios as will be seen later in a variant of the invention are chosen according to the intended purpose and the conditions of use of the latex particles. Briefly, the phenomenon of electronic energy transfer involves a donor molecule D* brought to an excited state by any form of radiation and an acceptor molecule $A_0$ in the ground state. Under certain conditions, if the energy level of D* is higher than or equal to that of A*, the energy initially acquired by the donor may be transmitted to the molecule A in order to form the excited species A*, without any direct excitation of $A_0$ having taken place.

The acceptor can then emit instead of the donor, at its intrinsic wavelength $\lambda$ (A). The normal emission of the donor (D*→D+hν) is replaced by:

1) $D^*+A_0 \rightarrow D_0+A^*$ (speed $K_T$) then
2) $A^* \rightarrow A_0+h\nu$ (emission of A at $\lambda$ (A)).

In the particular case of the fluorochrome pairs or trios presented here, the transfer takes place by resonance and involves a process of electromagnetic coupling through space which requires no contact between the donor and the acceptor. It is moreover necessary for there to be similarity in the energy level jumps (between the ground state and the excited state) for the donor-acceptor pair. There is thus an overlap between the emission spectrum of the donor D and the excitation spectrum of the acceptor A.

As a guide, mention may be made of the following fluorochrome pairs:

| D | | A |
|---|---|---|
| 9,10 DPA | $\rightarrow$ | 9,10 BPEA |
| 1,8 Cl$_2$-9,10 BPEA | $\rightarrow$ | 5,12-BPEN |
| 1,8 Cl$_2$-9,10 BPEA | $\rightarrow$ | TPP |
| Coumarin 153 | $\rightarrow$ | 1,8 Cl$_2$-9,10 BPEA |
| 9,10 DPA | $\rightarrow$ | Coumarin 153 |
| 1,8 Cl$_2$-9,10 BPEA | $\rightarrow$ | Nile red |
| 9,10 BPEA | $\rightarrow$ | Nile red |
| POPOP | $\rightarrow$ | Coumarin 153 |
| 9,10 BPEA | $\rightarrow$ | TPP |

The pairs formed from the abovementioned fluorochromes are advantageous in many respects.

They are commercial products. They are insoluble in water and are chemically and photochemically stable. Since they are compatible with the latex polymers, when they are incorporated therein they lead to markers having an unexpected sensitivity which is of significantly higher performance than that of conventional markers.

The latex particles containing the said fluoro-chromes conventionally consist of polymers obtained by polymerization of ethylenically unsaturated monomers. Such a polymer is a homopolymer or copolymer containing units derived from vinylaromatic or ethylenic monomers, or from alkanoic or ethylchic acids or esters, which are optionally functionalized.

This type of polymer [sic] is readily accessible to any person skilled in the art and it will be sufficient to mention only a few such polymers [sic] below, in a non-limiting manner. These may be:
- ethylenic monomers of isoprene, 1,3-butadiene, vinylidene chloride or acrylonitrile type,
- vinylaromatic monomers such as styrene, bromo-styrene, alpha-methylstyrene, ethylstyrere[sic], vinyl-toluene, chlorostyrene or chloromethylstyrene, or vinyl-naphthalene,
- alkanoic acids, esters or anhydrides such as acrylic acid, methacrylic acid, alkyl acrylates and alkyl methacrylates in which the alkyl group possesses 3 to 10 carbon atoms, hydroxyalkyl acrylates, acrylamides, ethylenic acid esters containing 4 or 5 carbon atoms, and
- difunctional monomers such as divinylbenzene or 2,2-dimethyl-1,3-propylene diacrylate and/or other water-insoluble copolymerizable monomers.

The monomers may bear anionic or cationic groups of sulfate, sulfonate, phosphonate or quaternary ammonium type. They may also be groups capable of reacting, directly or indirectly, with functional groups of amine type, for example, borne by biological molecules such as proteins and enzymes. Representative examples of these functional groups which may be mentioned are halogens, carboxyl, amine, isocyanate, aziridine, aldehyde and sulfonyl groups and epoxy and chloromethyl functions.

The monomers more particularly used within the context of the present invention belong to the arylene and/or alkylene family. They are preferably vinylaromatic compounds such as: styrene, alpha-methylstyrene, ethyl-styrene, tert-butylstyrene and vinyltoluene. These monomers are preferably substituted with one or more functional groups of halogen, amine, alkoxy, carboxyl and/or sulfonyl type.

These monomers are used alone or mixed with each other in any proportion, or alternatively mixed with another copolymerizable monomer chosen from those mentioned above.

The polymer particles may be obtained by the use of any polymerization technique such as conventional emulsion polymerization, microemulsion, suspension or microsuspension polymerisation or, where appropriate, by polymerization in an organic medium. These techniques, which are familiar to those skilled in the art, will not be redescribed here.

The particles, containing the fluorescent latex according to the invention, are hydrophobic and preferably have a size generally of between 0.01 and 20 microns and preferably less than 5 microns. They are calibrated, monodispersed and present in the latex at a proportion ranging between 0.05 and 10% by weight relative to the total weight of the latex, preferably between 0.1 and 1%.

According to a first advantageous variant, the fluorescent latex is characterized in that the emission of the fluorochrome D makes it possible to excite the fluorochrome A directly, the emission spectrum of the fluorochrome D partially overlapping the excitation spectrum of the fluorochrome A.

For at least 10%, preferably at least 50%, by weight of the particles the A:D molar ratios is preferably greater than 1, advantageously greater than 1.2.

The A:D ratio is advantageously greater than 1, preferably greater than 1.2. It has indeed been found, surprisingly, that latex particles having such a ratio led to a phenomenon of amplification of the intensity of the emission signal.

According to another advantageous variant, the fluorescent latex is characterized in that the emission of the fluorochrome D makes it possible to excite the fluorochrome A indirectly, the latex particles containing at least one intermediate fluorochrome I whose excitation spectrum partially overlaps the emission spectrum of D and the emission spectrum partially overlaps the excitation spectrum of A.

The A:I and I:D molar ratio [sic] will preferably always be greater than 1, preferably $\geq 1.2$. Latex particles having such a ratio also lead to an amplification of the intensity of the emission signal.

The use of a trio makes it possible to shift the emission wavelength of the latex even further and consequently to avoid any interference with even more certainty and moreover avoids the overlapping of the emission spectrum A with the excitation spectrum of D, thereby rendering the quantification even more precise.

Among the trios which may be used in the context of the present invention, the following may be mentioned as guides:

| D | I | A |
|---|---|---|
| POPOP | Coumarin 153 | 1,8 Cl$_2$-9,10 BPEA |
| 9,10 DPA | 9,10 BPEA | Nile red |
| Coumarin 153 | 1,8 Cl$_2$-9,10 BPEA | TPP |
| Coumarin 153 | 1,8 Cl$_2$-9,10 BPEA | 5,12-BPEN |

It is possible with the latex according to the invention to arrive at detection thresholds very much lower than $10^{-12}$ mol of particles per liter under the fluorescence measurement conditions described below.

It is thus possible to obtain detection thresholds ranging from $10^{-14}$ to $10^{-17}$ mol of particles per liter.

The fluorescent latices according to the invention may be used in all the conventional applications of latices which are well known to those skilled in the art (paint, etc.).

The fluorescent latices according to the invention are more particularly intended for direct or indirect involvement in biological analyses. They may be used, for example, as reagents in immunological tests, as scintillators, as calibration standards in flow cytofluorimetry for example, or alternatively as cell markers. In the latter case, phagocytosis of the particles of a fluorescent latex by the cells to be studied is effected.

The subject of the invention is thus the applications of the fluorescent latices in the biological field. These applications usually require the prior binding of an immunoreactive species to the latex.

The subject of the invention is consequently fluorescent latices functionalized with at least one inunmunoreactive species..

A fluorescent latex is coupled with an immuno-reactive species via one or more reactive functional group(s) present at the surface of these particles.

The standard procedure for performing this type of coupling involves the creation of a covalent bond to this immunoreactive species, by simple chemical reaction. The chemical groups present at the surface of the particles may either react directly with the immuno-reactive compounds bearing free sulfhydryl or amino functions, or indirectly after activation. Functional groups which may be mentioned in particular are carboxyl, haloalkyl, alkylsulfonyl and vinylsulfonyl groups. In the case of aldehyde and epoxy groups, these may be activated chemically beforehand in order to lead to a function having a higher activity towards the immunoreactive species.

The term immunoreactive species is understood to cover any chemical or biological compound bearing at least one site capable of complexing with another specific so-called receptor molecule. Examples of immuno-reactive species which may be mentioned are primary amines, amino acids, peptides, proteins, lipoproteins or microorganisms of viral or bacterial type, for example. It may also be an antibody or an enzyme. This immuno-reactive species has the essential mission of reacting with another species, either by simple biological affinity or by chemical reaction, becoming complexed via one of its functions to a receptor site of the species to be assayed.

These immunoreactive species are added to the fluorescent latex particles according to standard procedures, using known reactions which will not be redescribed here.

The functionalized fluorescent latices find an application in the field of immunological assaying. The latices functionalized with a specific antibody are thus capable of recognizing the complementary antigens present in a biological fluid such as blood or urine. The diagnosis depends on the recognition or non-recognition of the antigens. This result may be quantified by the intensity of the signal, which depends on the antigen concentration.

Fluorescent latices also find an application in cell marking. In this case, an immunoreactive species grafted onto the fluorescent latices reacts with one or more antigens on a cell surface and allows its presence to be detected by fluorescence.

Mention may be made, for example, of the detection of cancer cells which lead, for example, to an increase in the number of EGF (Epidermal Growth Factor) receptors.

This technique also makes it possible to detect an increase in the level of nucleic acid or an increase in cell volume.

The latices according to the present invention also find an advantageous application in flow cytofluorimetry, which makes it possible to perform quantitative measurements on a large number of cells, but which are analyzed individually. For each cell, it is possible to determine its volume, its size and, in the presence of specific fluorescent markers, the level of DNA and RNA therein as well as the presence of membrane antigens or other receptors, for example. In combination with this analytical capacity, the physical and selective separation of cell subpopulations based on parameters determined beforehand by the user amplifies the value of this technique.

The invention also relates to a process for the preparation of the fluorescent latices described above.

The preparation process is characterized in that one and/or other of the following steps is (are) carried out:

introduction, during the polymerization of the monomer (s) intended to constitute the latex particles, of one or more of the fluorochromes D, A and optionally I in suspension in a fraction of the monomer or of one of the monomers, mixing of one or more of the fluorochromes D, A and optionally I, solubilized in a non-aqueous solvent, with an aqueous dispersion of latex particles.

The two steps will be carried out successively when, on account of the chosen process, it has not been possible by one of the two steps to include the various fluorochromes into the latex particles.

Thus, when only one of the fluorochromes is introduced during the polymerization, it will be necessary in a second step to mix the other fluorochrome in a non-aqueous solvent with the aqueous dispersion of latex particles which is obtained after polymerization.

In another case, it will be possible to introduce the various fluorochromes into the step of mixing (or swelling) of the latex.

The first step is generally referred to as the overpolymerization step whereas the second step is referred to as the solvent swelling step.

In a known manner, the fluorescent latex particles obtained after one and/or other of these two methods are then characterized in terms of level of fluorochromes contained, of residual fluorescence in the supernatant and of sensitivity of detection of the emission of fluorescence.

The maximum hydrophobic fluorochrome content in the latex particles obviously depends on the nature of the fluorochromes, the insertion technique used, the nature of the polymer constituting the particles and the size of these particles. This content may thus vary considerably and reach values of several million fluoro-chrome molecules per latex particle.

As a guide, for a particle with a diameter of 0.3 μm, this content ranges from 10,000 to 400,000, preferably between 60,000 and 350,000, fluorochrome molecules per latex particle.

Incorporation of the fluorochromes inside the particles, according to one and/or others [sic] of the two abovementioned techniques, is advantageous in two respects:

It makes it possible to be completely free of any phenomenon of release of the fluorochromic agent while assaying. No phenomenon of so-called residual fluorescence is noted in the supernatant. This results in increased reliability of the assay technique.

The external surface of the latex particles remains available for chemical or biochemical couplings.

An important advantage of fluorescence over other techniques such as UV-visible or radioactive emission is to make it additionally possible to assay inhibitory compounds. This characteristic offers additional practical applications to the fluorescent latices according to the invention, such as the assaying of traces of heavy metals, of oxygen, etc. This technique already forms the subject of applications in immunology. This relates more particularly to the method of reverse immunofluorescence.

The examples presented below will make it possible to demonstrate other advantages and characteristics of the present invention without, however, limiting the scope thereof.

The fluorescent latices forming the subjects of the examples below were characterized by their fluorescence emission detection threshold and, for the respective particles thereof, by their fluorochrome content, according to the following methods:

A—Measurement of the Fluorescence Detection Threshold

This consists in determining the minimum concentration of particles which can be detected by the fluorimeter under conditions which are acceptable in terms of the signal/noise ratio (>10), by a conventional fluorimeter and without deoxygenation of the medium. This conventional fluorimeter comprises a polychromatic light source (150 W xenon lamp), grating monochromators, a standard detector and a device for reading and/or recording an induced photocurrent. It does not contain any specific additional signal processing device. It is clear that this minimum detectable concentration depends highly on the analysis conditions.

Consequently, the values indicated in the examples below, determined under standard conditions, should be considered as being indicative of the minimum performance levels of the fluorescent latices analyzed.

To do this, a study is performed on the intensity emitted as a function of the dilution of the starting latex, at precise excitation and emission wavelengths and for predefined and preset optical or electronic parameters of the fluorimetry.

The value of the minimum concentration is deduced from reading the corresponding intensity/concentration curve.

B—Determination of the Fluorochrome Content of a Particles [sic]

This content may be determined by dissolving a known weight of dry latex in a common solvent for the polymer and for the fluorochrome. This solvent is generally toluene. The fluorochrome concentration is then determined by UV-visible absorption. The particle concentration is deduced by calculating, on the basis of the weight of dry polymer, the particle size and the density of the polymer.

The content $\eta p$ is then given by the ratio:

$$\eta p = \frac{\text{fluorochrome concentration}}{\text{particle concentration}}$$

EXAMPLE 1

Preparation of a Fluorescent Latex Marked with 9,10 DPA and with 9,10 BPEA

This fluorescent latex is prepared according to the swelling technique using the following reagents: Carboxylated polystyrene latex of diameter equal to 0.3 µm (123 g at a solids content of 8.13% by mass)

Toluene 15 g
Acetone 196 g
Potassium laurate 0.1 g
9,10 DPA 0.028 g
9,10 BPEA 0.032 g
20% $NH_4OH$, qs for pH=10.

The 9,10 DPA is dissolved in 7.5 g of toluene, followed by addition of acetone (98 g). The pH of the latex is adjusted to a value of 10 using $NH_4OH$. The potassium laurate is then added to the latex and the mixture is homogenized for a few minutes with stirring. The fluorochrome solution is then added slowly to the latex. The resulting suspension is stirred for 3 hours at 40° C. The organic solvents are then removed by distillation as slowly as possible. Deionized water is added during the distillation so as to adjust the solids content to about 5%.

The 9,10 BPEA is dissolved in the remaining toluene, followed by addition of acetone (98 g g[sic]). The pH of the latex is then readjusted to a value of 10 using $NH_4OH$. The fluorochrome solution is then added slowly to the latex. The resulting suspension is stirred for 3 hours at 40° C. The organic solvents are then removed as above. The final solids content (SC) by weight is close to 5%. The fluorescent latex thus obtained is washed by ultrafiltration.

The latex obtained has the following characteristics:
9,10 DPA (donor): 84,000 labels/particle, i.e. 0.25 weight % polymer.
Insertion yield: 83%.
9,10 BPEA (acceptor): 123,000 labels/particle, i.e. 0.3 weight % polymer.
Insertion yield: 100%.
The acceptor/donor marking ratio is 1.5.

The photoinduced fluorescence was then measured using the experimental device comprising a polychromatic light source (150 W xenon lamp), grating monochromators, a standard detector and a device for reading and/or recording the signal.

When excited at 360 nm (region at which the absorption of the 9,10 DPA is 8 times greater than that of 9,10 BPEA), the emission spectrum of the latex is virtually reduced to the emission of the 9,10 BPEA (max: 480 and 510 nm). The emission of the 9,10 DPA (max: 410 and 430 nm) is virtually nonexistent (1/20th of that of the 9,10 BPEA).

The excitation was recorded for the emission at 550 nm (where the fluorescence of the 9,10 DPA is negligible). The spectrum shows distinct shoulders corresponding to the peaks characteristic of the excitation of 9,10 DPA.

For three different latices (9,10 BPEA alone, 9,10 BPEA and 9,10 DPA separately, and 9,10 BPEA and 9,10 DPA in the same particle) the ratio of the intensity I emitted at 515 nm (where the emission of 9,10 BPEA is in majority) is then estimated for excitations at 440 nm (excitation of 9,10 BPEA alone) and at 360 and 375 nm (simultaneous excitation of 9,10 DPA and 9,10 BPEA). Under these conditions, an energy transfer from 9,10 DPA to 9,10 BPEA should be reflected in a substantial increase in the ratios I(360)/I(440) and I(375)/I(440).

The following results are observed:
a) Latex of 9,10 BPEA alone: I(360)/I(440)=0.06
I(375)/I(440)=0.12
b) 9,10 BPEA and 9,10 DPA in separate particles (mixture of latices)
I(360)/I(440)=0.07
I(375)/I(440)=0.13.

The results are equivalent to a). No interaction is observed between 9,10 DPA and 9,10 BPEA.

c) 9,10 BPEA and 9,10 DPA in the same particle.

I(360)/I(440)=0.22

I(375)/I(440)=0.36.

Thus, in the latter case, there is indeed an increase by a factor of 3 in the emission of 9,10 BPEA, excited in the absorption region of 9,10 DPA when the two labels are located in the same particle.

This is thus effective proof of a transfer of energy from 9,10 DPA to 9,10 BPEA.

Under these conditions (excitation at 375 nm and emission at 480 nm), the fluorescence detection threshold of the sample is equal to $5 \cdot 10^{-15}$ mol of particles per liter.

EXAMPLE 2

Preparation of a Fluorescent Latex Marked with 1,8 $Cl_2$-9,10 BPEA and with 5,12-BPEN The fluorescent latex is prepared according to Example 1 using the following reagents:

Latex according to Example 1

1,8 $Cl_2$-9,10 BPEA 0.028 g 5,12-BPEN 0.032 g

Toluene 10.25 g

Acetone 196 g

Potassium laurate 0.1 g

20% $NH_4OH$, qs for pH=10

The latex obtained has the following characteristics:

1,8 $Cl_2$-9,10 BPEA 77,000 labels/particle, i.e. 0.29% of the weight of the polymer 5,12-BPEN 88,000 labels/particle, i.e. 0.32% of the weight of the polymer.

The acceptor/donor marking ratio is 1.15.

Irrespective of the length of order [sic] of excitation between 470 and 515 nm, the emission of the latex only reduces to that of the BPEN (570 nm).

The ratio of the intensity emitted at 620 nm (emission of the BPEN) is then estimated for excitations at:

550 nm (absorption of the BPEN alone)

470 nm (simultaneous absorption of 5,12-BPEN and 1,8 $Cl_2$-9,10 BPEA)

440 nm (dominant absorption of the 1,8 $Cl_2$-9,10 BPEA alone).

The following intensity ratios are obtained:

I(470)/I(550)=1.47

I (440)/I(550)=0.52.

Whereas, for a latex comprising only the 5,12-BPEN the intensity ratios are respectively:

I(470)/I(550)=0.32

I (440)/I (550)=0.08.

The detection limit [sic] threshold was then measured, which is $6-10^{-15}$ M of particles/L.

Consequently, the fluorescence equivalent to one latex particle is 158,000 molecules of 5,12-BPEN, i.e. close to twice the actual marking of the latex with 5,12 BPEN.

Although the 5,12-BPEN is the only species to emit, this equivalent fluorescence is close to the total number of labels involved. The overall efficiency of this double marking is 0.96 and is thus comparable with that of a latex monomarked with 5,12-BPEN or with 1,8 $Cl_2$-9,10 BPEA alone.

EXAMPLE 3

Preparation of a Fluorescent Latex Marked with 9,10 BPEA and with 1,8 $Cl_2$-9,10 BPEA The fluorescent latex is prepared according to Example 1 using the following reagents:

Latex according to Example 1

9,10 BPEA 0.028 g 1,8 $Cl_2$-9,10 BPE 0.032 g

Toluene 15 g

Acetone 196 g

Potassium laurate 0.1 g

20% $NH_4OH$, qs for pH=10

The latex obtained has the following characteristics:

9,10 BPEA: 105,000 labels/particle, i.e. 0.34% of the weight of the polymer 1,8 $Cl_2$-9,10 BPEA 107,000 labels/particle, i.e. 0.40% of the weight of the polymer.

The acceptor/donor marking ratio is 1.02.

Under excitation at 400 nm (at which wavelength the light is practically absorbed by the 9,10 BPEA), the emission is practically reduced to the 1,8 $Cl_2$-9,10 BPEA ($\lambda$max: 530 nm/1/2 intensity at 565 nm).

The ratio of the intensity emitted at 600 nm (emission of the 1,8 $Cl_2$-9,10 BPEA) is then estimated for excitations at:

500 nm (absorption of the 1,8 $Cl_2$-9,10 BPEA alone)

440 nm (simultaneous absorption of 9,10-BPEA and 1,8 $Cl_2$-9,10 BPEA)

400 nm (dominant absorption of the 9,10 BPEA).

The following intensity ratios are obtained:

I(440)/I(500)=1.4

I(400)/I(500)=0.47.

Whereas, for a latex comprising only the 1,8 $Cl_2$-9,10 BPEA the intensity ratios are respectively:

I(440)/I(500)=0.45

I(400)/ (500)=0.11.

The detection limit [sic] threshold was then measured, which is $2-10^{-15}$ M of particles/L for an excitation at 470 nm and an emission at 530 nm.

Consequently, the fluorescence equivalent to one latex particle is 211,000 molecules of 1,8 $Cl_2$-9,10 BPEA, i.e. twice the actual marking of the latex with 1,8 $Cl_2$-9,10 BPEA.

This equates to the total number of labels inserted, leading to an overall fluorescence efficiency equal to 1.0.

We claim:

1. Fluorescent latex the particles of which contain at least one hydrophobic fluorochrome A (acceptor) and at least one hydrophobic fluorochrome D (donor) which are encapsulated, A being different from D and the emission of the fluorochrome D making it possible, under the action of light radiation, to excite the fluorochrome A.

2. Fluorescent latex of claim 1, wherein the emission of the fluorochrome D makes it possible to excite the fluorochrome A directly, the emission spectrum of the fluorochrome D partially overlapping the excitation spectrum of the fluorochrome A.

3. Fluorescent latex of claim 2, wherein for at least 10% by weight of the particles, the A:D molar ratio is greater than 1.

4. Fluorescent latex of claims 2 or 3, wherein the fluorochromes A and D are chosen from condensed, polyaromatics, tetraphenylporphine and one of the organometallic complexes thereof.

5. Fluorescent latex of claim 4, wherein the fluorochromes A and D are chosen from 9,10 diphenyl-anthracene (9,10 DPA), 9,10 bis-phenyl-ethynyl-anthracene (9,10 BPEA), 1,8 dichloro 9,10 bis-phenyl-ethynyl-anthracene (1,8 $Cl_2$-9,10 BPEA), 5–12 bis-phenyl-ethynyl-naphthacene (5,12 BPEN), 6,13-bis (phenyl-ethynyl) pentacene, tetrabenzo(de, hi,op,st)pentacene, Coumarin 153, Nile red, 1,4-di[2(5-phenyloxazolyl)]-benzene (POPOP), [1,4-di[2-(4-methyl-5-phenyloxazolyl)]-benzene 1,4-di[4-methyl-5-phenyl-2-oxazolyl]benzene, and tetraphenylporphyrine (TPP).

6. Fluorescent latex of claim 5, wherein the fluorochromes A and D are chosen from the following pairs:

| D | A |
|---|---|
| 9,10 DPA | 9,10 BPEA |
| 1,8 $Cl_2$-9,10 BPEA | 5,12-BPEN |
| 1,8 $Cl_2$-9,10 BPEA | TPP |
| Coumarin 153 | 1,8 $Cl_1$-9,10 BPEA |
| 9,10 DPA | Coumarin 153 |
| 1,8 $Cl_2$-9,10 BPEA | Nile red |
| 9,10 BPEA | Nile red |
| POPOP | Coumarin 153 |
| 9,10 BPEA | TPP |

7. Fluorescent latex of claim 1, wherein the emission of the fluorochrome D makes it possible to excite the fluorochrome A indirectly, the particles of the latex containing at least one intermediate fluorochrome I whose excitation spectrum partially overlaps the emission spectrum of D and the emission spectrum partially overlaps the excitation spectrum of A.

8. Fluorescent latex of claim 7, wherein the molar concentration ratios A:I and I:D are greater than 1.

9. Fluorescent latex of claims 7 or 8, wherein the fluorochromes are chosen from the following trios:

| D | I | A |
|---|---|---|
| POPOP | Coumarin 153 | 1,8 $Cl_2$-9,10 BPEA |
| 9,10 DPA | 9,10 BPEA | Nile red |
| Coumarin 153 | 1,8 $Cl_2$-9,10 BPEA | TPP |
| Coumarin 153 | 1,8 $Cl_2$-9,10 BPEA | 5,12-BPEN |

10. Fluorescent latex of claims 7 or 8, wherein when they are subjected to an excitation using a light radiation, the emission spectrum of the particles does not overlap the excitation spectrum of the said particles.

11. Fluorescent latex of claim 1, wherein when they are subjected to a light radiation, the detection threshold of the particles is less than or equal to $10^{-12}$ mol of particles per liter.

12. Fluorescent latex of claim 1, wherein its particles are between 0.01 micron and 20 microns in size.

13. Fluorescent latex of claim 1, wherein the particles constitute between 0.05 and 10% of its weight.

14. Fluorescent latex of claim 1, wherein the polymer constituting its particles is a homopolymer or copolymer containing units derived from vinylaromatic or ethylenic monomers or from alkanoic or ethylenic acids or esters, which are optionally functionalized.

15. Fluorescent latex of claim 1, wherein it is functionalized with at least one immunoreactive species.

16. A method of using the fluorescent latex of claim 15 as a reagent in immunological tests, in reverse immunofluorescence, as a scintillator, as a calibration standard in flow cytofluorimetry and/or as cell markers.

17. Process for the preparation of a latex of claim 1, comprising at least one of the following steps:

introducing, during the polymerization of the monomer(s) intended to constitute the latex particles, of one or more of the fluorochromes D, A and optionally I in suspension in a fraction of the monomer or of one of the monomers, and mixing of one or more of the fluorochromes D, A and I, solubilized in a non-aqueous solvent, with an aqueous dispersion of latex particles.

18. Fluorescent latex of claim 3, wherein the A:D molar ratio is greater than 1.2.

19. Fluorescent latex of claim 7, wherein the molar concentration ratios A:I and I:D are greater than 1.2.

* * * * *